United States Patent [19]

Schwartz

[11] 4,084,246
[45] Apr. 11, 1978

[54] PULSE GENERATOR

[75] Inventor: Arnold Schwartz, Bridgeport, Conn.

[73] Assignee: The Perkin-Elmer Corporation, Norwalk, Conn.

[21] Appl. No.: 772,223

[22] Filed: Feb. 25, 1977

Related U.S. Application Data

[63] Continuation-in-part of Ser. No. 733,713, Oct. 18, 1976, abandoned.

[51] Int. Cl.² ............... G06F 15/46; H03B 19/00; G05D 11/02
[52] U.S. Cl. ............... 364/510; 137/101.19; 307/271; 328/39; 328/62; 364/701; 364/703; 417/338
[58] Field of Search ........... 235/150.3, 151.3–151.35; 417/338; 137/87, 88, 98, 101.19; 328/38, 39, 48, 62, 180; 307/271, 225 R

[56] References Cited

U.S. PATENT DOCUMENTS

| | | | |
|---|---|---|---|
| 3,219,046 | 11/1965 | Waugh | 137/101.19 |
| 3,229,077 | 1/1966 | Gross | 137/101.19 |
| 3,272,217 | 9/1966 | Young | 137/101.19 |
| 3,398,689 | 8/1968 | Allington | 417/338 |
| 3,764,790 | 10/1973 | Long et al. | 235/150.3 |
| 3,866,129 | 2/1975 | Cornelissen | 307/271 |
| 3,885,142 | 5/1975 | Ninke et al. | 235/150.3 |
| 3,992,612 | 11/1976 | Dunn | 235/150.3 |

Primary Examiner—Felix D. Gruber
Attorney, Agent, or Firm—S. A. Giarratana; F. L. Masselle; J. D. Crane

[57] ABSTRACT

A pulse generator for producing two output pulse trains A and B where the total number of pulses in both train A and B over a fixed time period remains a constant. The two pulse trains are derived from a master clock which gates a plurality of cascade connected synchronous decade rate multipliers. A selector is set either statically or dynamically to the value N where N is the number of pulses desired in one pulse train out of every M pulses produced by the master clock. A summing means is coupled to all the multipliers to produce a first intermediate pulse train with N pulses for every M clock pulses. A difference means is coupled to each multiplier and to the master clock to produce a pulse in a second intermediate pulse train every time a clock pulse occurs and a pulse in the first pulse train does not occur. A pulse counter is coupled to each intermediate pulse train output to produce two output pulse trains A and B each having a substantially constant pulse frequency.

30 Claims, 7 Drawing Figures

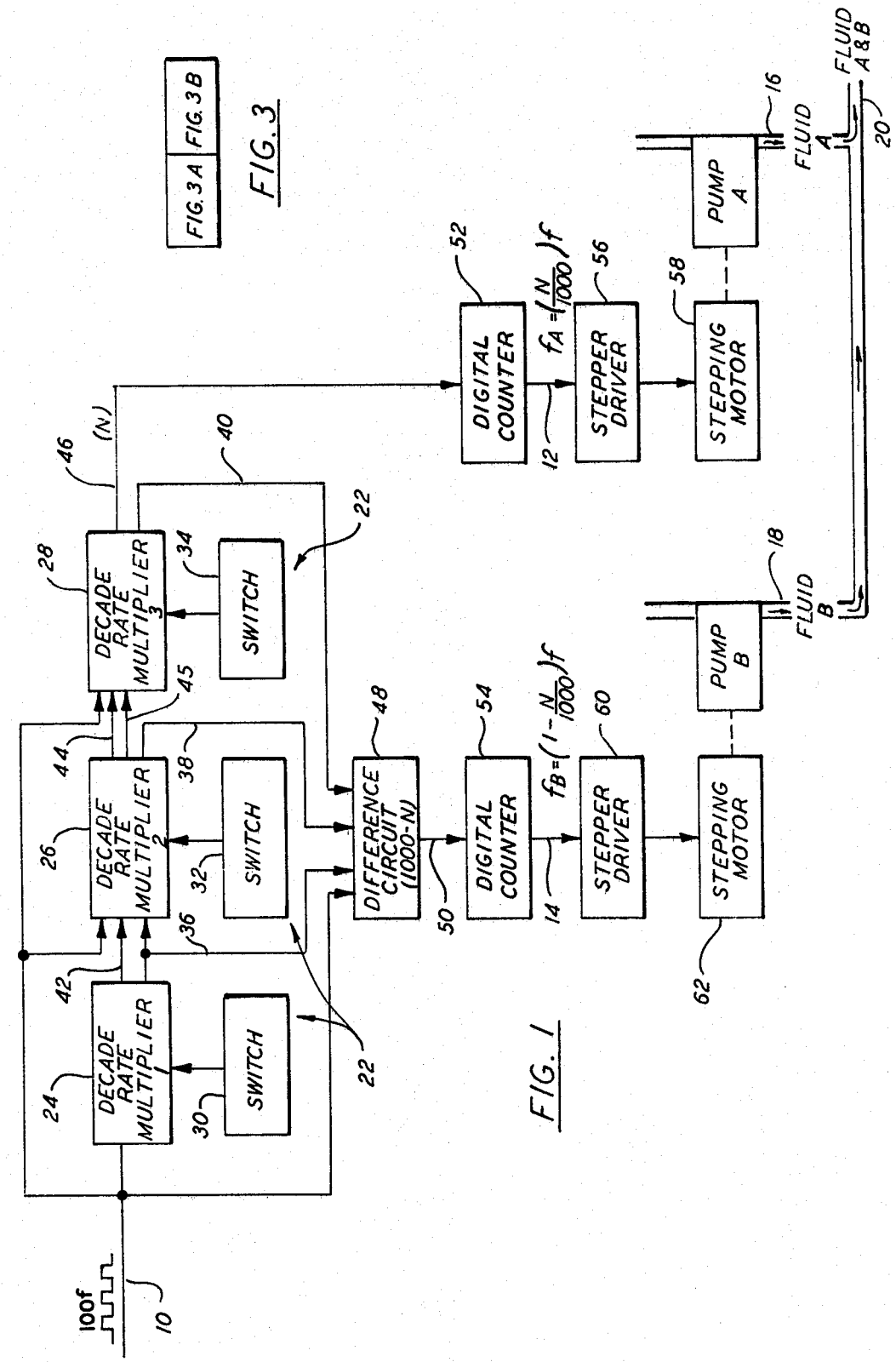

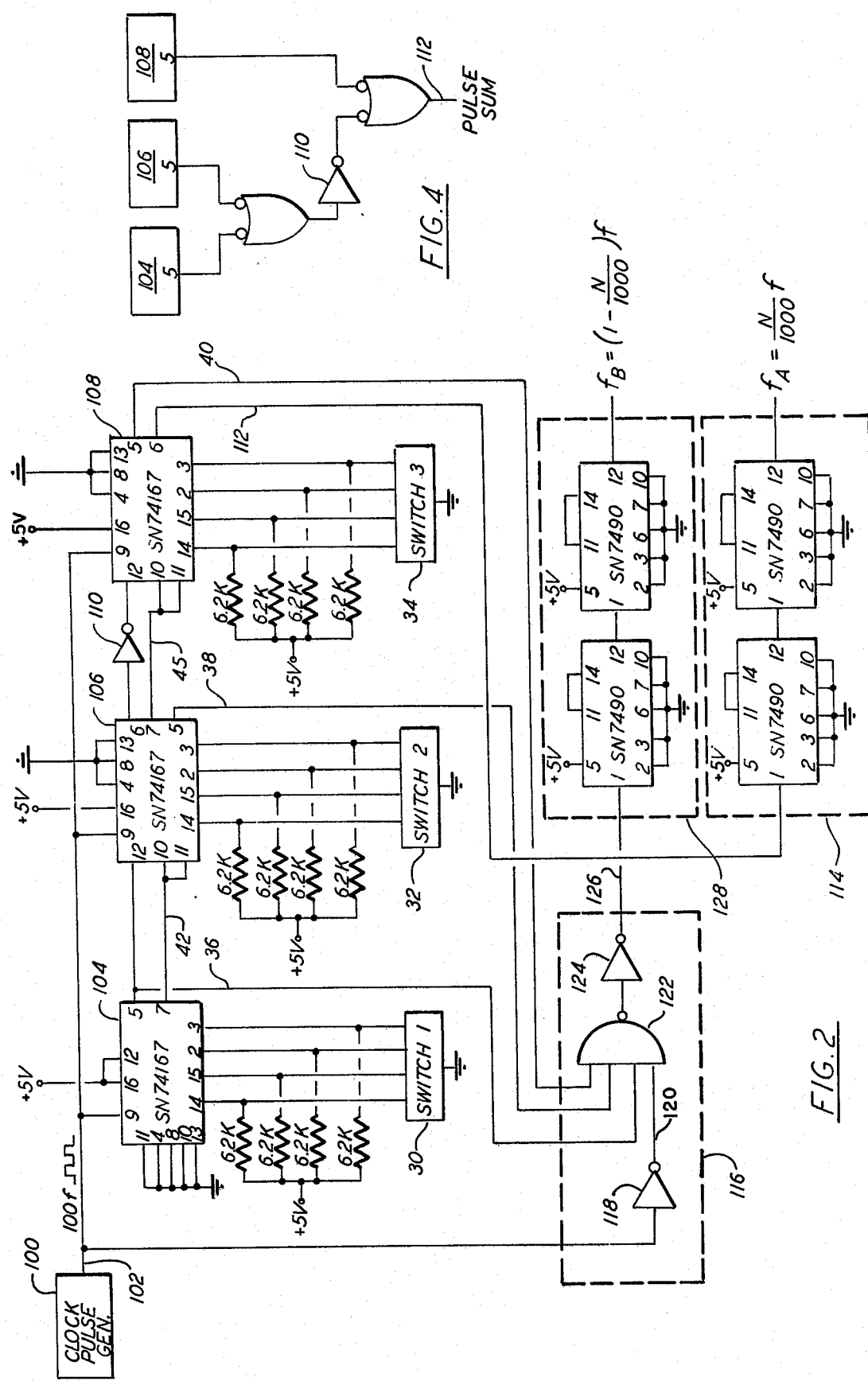

PULSE GENERATOR

BACKGROUND OF THE INVENTION

This application is a continuation-in-part of Patent Application Ser. No. 733,713 filed Oct. 18, 1976, now abandoned.

The invention relates broadly to the field of pulse generators and particularly to a generator for producing two pulse trains where the sum of the pulses in both pulse trains over a given period of time is a constant.

The invention is particularly adapted for use in a liquid chromatograph although it may be used in other devices where one desires to control the percent of component A in a two component solution where the sum of the two components in a given volume is a constant i. e., the % A in A + B equals a constant. In a liquid chromatograph, the invention has particular application in controlling the flow rate of two solvents where it is desired to maintain the total flow of the two solvents constant while permitting precise control of the percent of one solvent in the mixture.

In the prior art, various devices have been developed for producing a constant total flow while controlling the flow rate of two constituents. One approach relies on first starting two pumps and analyzing the mixed output solution from both pumps to determine the concentration of each component. Thereafter, the rate of at least one pump is adjusted to thereby change the concentration of one fluid component. Other apparatus is provided to maintain the sum of fluid flow through the two pumps at a constant. This apparatus is quite complicated because it relies on dynamic feedback to control fluid flow through the pumps and other controls to maintain total flow at a constant.

Other approaches have been tried in other devices for maintaining the total flow of two fluids at a constant rate while permitting the percent of one fluid in the total to be controlled. One such approach is described in U.S. Pat. No. 3,398,689. In the apparatus of that patent, the speed of two motors which power two pumps is controlled by an electrical circuit with the control signals being derived from a programming mechanism. The programming mechanism comprises a set of potentiometers whose wipers are connected in sequence to voltage controlled oscillators, the first oscillator produces pulses at a maximum rate, while the second oscillator produces pulses at a minimum rate, both in response to a maximum wiper voltage. The second oscillator produces pulses at a maximum rate and the first oscillator produces pulses at a minimum rate in response to a minimum potentiometer wiper voltage. The oscillator pulses drive the pump motors at a speed proportional to the pulse rate.

While the approach described in the above mentioned patent generally functions well, it does suffer from many problems typical to analog systems, i.e., the apparatus has resolution, drift and linearity problems. Indeed, many of the problems are directly attributable to the fact that two independent voltage controlled oscillators are used each to produce a signal for driving one of the pump motors. Since the oscillators are independent circuits, the output frequency of each is difficult to precisely control and they cannot be precisely synchronized with each other. Hence, the pumps controlled thereby do not necessarily maintain the same total flow when the speed of each is changed.

In the above mentioned patent, large changes in total flow rate are accomplished by changing gears located between the drive motors and the pumps. Accordingly, there is a considerable period of time, expense and inconvenience required to convert the patented apparatus to operate at a different total flow rate. Dynamic total flow rate change is impossible to achieve with this device.

Accordingly, it is a principal object of the invention to provide a pulse generator for control of two pumps or the like which is simple in design and does not suffer from linearity, drift or resolution problems.

It is another object of the invention to provide a pulse generator for controlling the total number of pulses in two pulse trains over a fixed period of time wherein the total number of pulses is more accurately maintained then by prior analog controllers.

It is still another object of the invention to provide a pulse generator for dynamically controlling the total number of pulses produced in two pulse trains over a fixed period of time while also maintaining dynamic control over the pulse rate of each pulse train.

It is still a further object of the invention to provide a pulse generator useful for controlling two pumps wherein the total flow from both pumps is a dynamically selectable constant and the percent of fluid pumped by one of the pumps in the total flow is directly and dynamically adjustable.

It is still a further objective of the invention to provide a pulse generator for finely controlling the flow rate of two pumps so that the combined flow rate of both pumps is a selectable constant which can be duplicated with different systems regardless of operating characteristic differences between the nomimally identical pumps of the different systems which usually arises from physical differences therebetween.

BRIEF DESCRIPTION

The invention includes a master clock for producing a pulse train at a selectable rate which, for an illustrative application of the invention, is proportional to the total flow rate of two fluids. The oscillator pulses are coupled to a plurality of synchronous decade rate multipliers connected in cascade. Each of the multipliers couples to a selector means to control the operation of each multiplier so that it produces M pulses, corresponding to the number set into the coupled selector means, for every 10 pulses input thereto while the rate multiplier is enabled. A summing circuit responds to all the multipliers to produce a first intermediate pulse train which corresponds to one pulse for each pulse produced by all the rate multipliers. A difference circuit, responsive to the master clock and to all the rate multipliers, produces a second intermediate pulse train where a pulse is produced each time a master clock pulse occurs and a pulse does not occur in the first intermediate pulse train.

Each intermediate pulse train passes through a pulse counter to obtain a more spectrally pure output pulse train. The total number of pulses in both output pulse trains over a fixed time period is a constant and the number of pulses in one output pulse train over the fixed time period is selectable by adjusting the selector means. For the later illustrated application of the invention, a pump responds to each output pulse train to pump a fluid at a rate proportional to the rate of pulses coupled thereto. Accordingly, the flow rate of each fluid is selectable within the constraint that the total flow of both fluids must remain a constant.

BRIEF DESCRIPTION OF THE DRAWINGS

The foregoing objects, advantages and features of the invention shall be described in greater detail below in connection with the drawings which show an illustrative application of the invention wherein:

FIG. 1 is a block diagram of the new pulse generator coupled to two pumps for pumping two fluids at a constant flow rate while controlling the constituent percentage;

FIG. 2 is a detailed circuit diagram of the new pulse generator;

FIG. 3 shows how

FIGS. 3A and 3B comprise a pulse diagram for representative pins in the circuit of FIG. 2; and FIG. 4 is a circuit diagram for the summing circuit of FIG. 2;

DETAILED DESCRIPTION

Figure 3A:
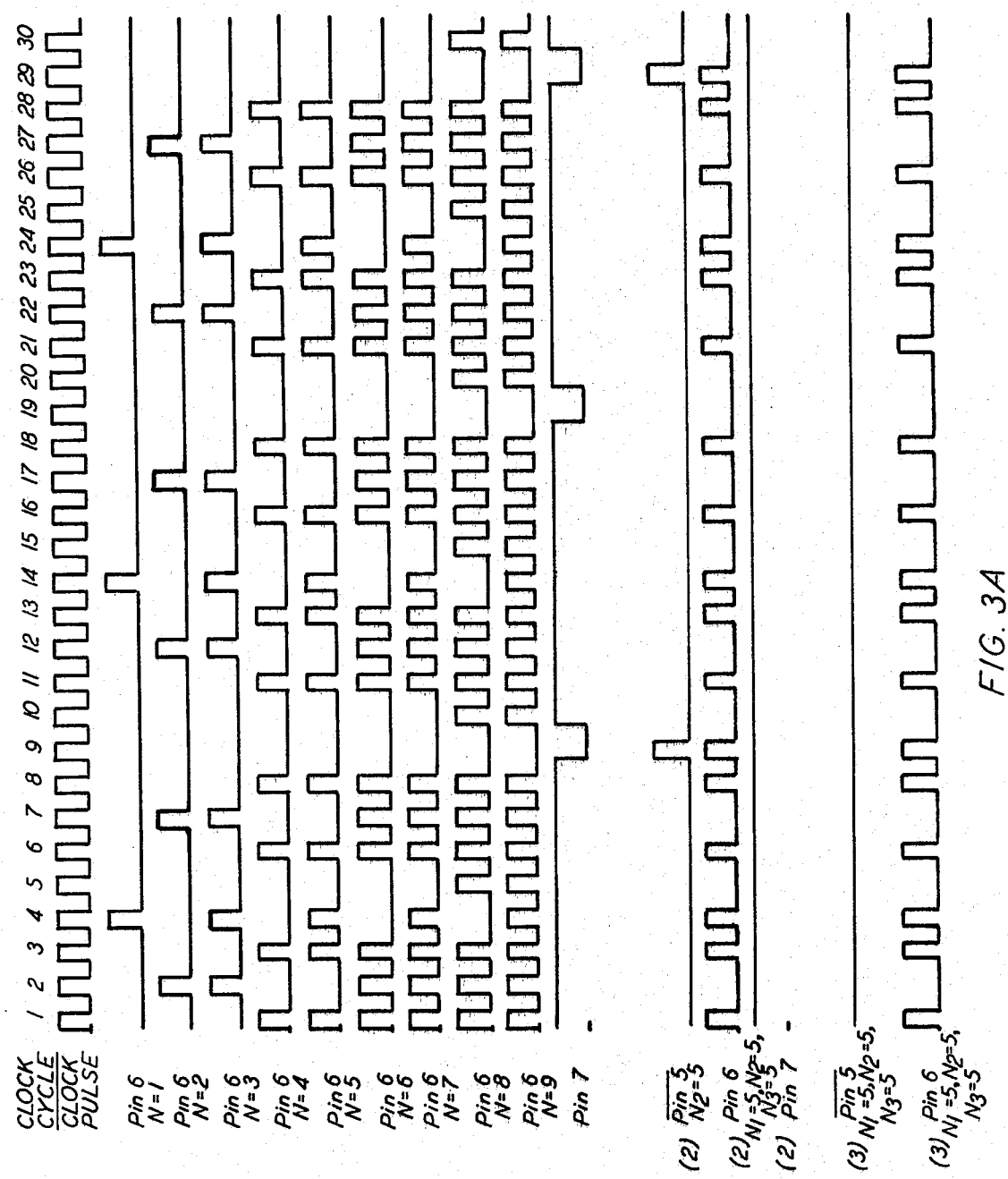
FIGS. 3A and 3B are positioned to form a pulse diagram.

Referring first to the block diagram of FIG. 1, an illustrative application of the invention is shown wherein an external pulse generator (not shown) supplies pulses on a line 10 which are converted into two output pulse trains A and B on output lines 12 and 14. These output pulse trains A and B respectively control pumps A and B for pumping fluid A and B respectively through conduits 16 and 18 which merge into a single conduit 20 where the flow rate of each pump is controlled by the frequency of pulses in the pulse train coupled thereto. In accordance with the principle of operation of the circuit in FIG. 1, the total flow rate of fluids A and B in conduit 20 is controlled by the rate of pulses input to the circuit at line 10. The percent of fluid A in the total fluid in conduit 20 is controlled directly by the setting of a selector, indicated generally at 22 which selects the number of pulses appearing in pulse train A and B over a fixed period of time.

The electronic circuitry of FIG. 1 includes three cascade connected decade rate multipliers 24, 26 and 28. Coupled respectively to these decade rate multipliers 24, 26 and 28 are three digit switches 30, 32 and 34 which are operative to produce a unique signal, transmitted to the decade rate multiplier coupled thereto, representative of the digit to which each respective digit switch is set and the set digits are related to the percent of fluid A in the flow of fluids A and B. In the illustrative embodiment of the invention, each digit switch 30, 32 and 34 is operative to produce a unique signal for each possible decimal digit between zero and nine to which the switch may be selectively set. Accordingly, the digit switches 30, 32 and 34 can be set to a number ranging from 0 to 999. For the embodiment shown, if the decimal number in the selector 22 is divided by 10, the resulting number corresponds identically to the percentage of fluid A in the total fluid flowing in conduit 20.

Alternatively, the selector switches 30, 32 and 34 can be replaced by a selector means responsive to an external condition or conditions to dynamically alter the unique signals coupled to the decade rate multipliers 24, 26, and 28. For example, the selector means may include one or more analog to digital converters for dynamically converting an external analog condition into a digital number whose magnitude is equivalent thereto. Alternatively, the selector means may comprise one or more digital counters or any other means producing a digital number. In this manner, the pulse generator can be made to produce a different number of pulses in each output pulse train over a given time period in response to dynamically changing conditions.

Each decade rate multiplier 24, 26 and 28 is operatively connected to receive pulses appearing on line 10 and respectively coupled to the digit switches 30, 32 and 34. Each decade rate multiplier 24, 26 and 28 is operative to respectively place on its output 36, 38 and 40 the same number of pulses as indicated by the setting of the coupled digit switch 30, 32 or 34 for each ten clock pulses appearing on line 10 for which the particular decade rate multiplier 24, 26 or 28 is enabled. By reason of the enabling circuitry, which will be described hereinafter in greater detail, the decade rate multiplier 24 is enabled during every clock cycle for the signal on line 10 where the time between the beginning of two successive pulses comprises a clock cycle, rate multiplier 26 is enabled for only one clock cycle for every 10 clock cycles appearing on line 10 and the decade rate multiplier 28 is enabled for only one clock cycle for every 100 clock cycles appearing on line 10. Accordingly, when each of the digit switches 30, 32 and 34 is set to a five, the following pulse strings are produced. For every ten pulses appearing on line 10, the decade rate multiplier 24 produces five pulses on its output line 36. For every 100 pulses on line 10, decade rate multiplier 26 produces 5 pulses on its output line 38. For every 1000 pulses on line 10, decade rate multiplier 28 produces 5 pulses on its output line 40. Thus, for every 1000 pulses on line 10, a total of 555 pulses are produced on these output lines 36, 38 and 40.

The decade rate multiplier 24 transmits enabling information on line 42 to the next cascade coupled data rate multiplier 26. The enabling information on line 42 is operative to enable the decade rate multiplier 26 to operate during one clock cycle out of every 10 clock cycles appearing on line 10. As will become clearer later, the cycle during which the decade rate multiplier 26 is enabled corresponds to a cycle when the decade rate multiplier 24 never produces a pulse on its output 36.

The decade rate multiplier 26 responds to the setting of the digit switch 32 to produce a corresponding number of pulses on its output line 38 for every ten pulses that it is enabled. Accordingly, when the digit switch 32 is set to a five, five pulses appear on the output line 38 for every 10 clock pulses input to the decade rate multiplier 26 while it is enabled. Therefore, the five pulses appearing at output line 38 occur over a period when 100 clock pulses occur at line 10.

Enabling information is transmitted from the decade rate multiplier 26 via the line 44 to control the operation of the next cascade coupled decade rate multiplier 28. The decade rate multiplier 28 responds to the enabling and data information so as to produce a number of pulses on its output line 40 corresponding to the setting of the digit switch 34 for every 10 pulses that the decade rate multiplier 28 is enabled. The enabling circuitry, as will be described hereinafter in greater detail, in decade rate multiplier 26 produces an enabling pulse which enables decade rate multiplier 28 to operate during only one clock cycle appearing at line 10 out of every 100 clock cycles. As will become clearer, the decade rate multiplier 28 is enabled at a time when neither decade rate multiplier 24 or 26 produces an output pulse. Accordingly, when the digit switch 34 is set to a five, the decade rate multiplier 28 produces five pulses on its output line 40 over a period of time corresponding to 1,000 pulses at line 10.

The circuitry of FIG. 1 includes a summing circuit to produce a pulse on the summing circuit output line 46 whenever a pulse appears on any of the decade rate multiplier output lines 36, 38 or 40. The summing circuit is internal to each of the decade rate multipliers 24, 26 and 28. As part of the summing circuit, the pulses transmitted over line 36 are transmitted to decade rate multiplier 26. Internal to the decade rate multiplier 26 is circuitry responsive to the pulses on line 36 and 38 to produce a pulse on line 45 during each clock cycle that a pulse appears at either output line 36 or 38. Internal to the decade rate multiplier 28 is circuitry responsive to pulses on line 45 and 40 to produce a first intermediate pulse train with a pulse on line 46 during each clock cycle that a pulse appears on line 45 or line 40, i.e., a pulse appears on line 46 during each clock cycle that a pulse appears on either line 36, 38 or 40 and for every 1000 pulses on line 10, N pulses appear on line 46 where N is the number set onto switches 30, 32 and 34. One circuit for accomplishing this summing function is described later in connection with FIG. 4.

The circuitry of FIG. 1 also includes a difference circuit 48 responsive to the clock pulses on line 10 and to the pulses appearing at the outputs 36, 38 and 40. The difference circuit 48 is operative to produce a second intermediate pulse train with a pulse at its output line 50 during each clock cycle for the pulses on line 10 when no pulse appears on any of the output lines 36, 38 or 40. Accordingly, for every 1,000 pulses appearing on line 10, (1,000 − N) pulses appear on line 50 where N is the number to which the switches 30, 32 and 34 are set.

Coupled to the output line 46 is a counter 52 which is operative to produce an output pulse train on line 12 wherein the time between pulses is substantially constant even though the time between pulses on line 46 is not constant. This is accomplished by a pulse counter which, for the illustrated embodiment of FIG. 1 is operative to place one pulse on the line 12 for every 100 pulses appearing on line 46.

Similarly, a counter 54 is coupled to the output line 50 from the difference circuit 48 and comprises, for the illustrated embodiment, a pulse counter which places a pulse at its output 14 for every 100 pulses appearing on line 50. Accordingly, the output pulse train on line 14 has a substantially constant time period between pulses.

By reason of the counting and the summing and difference operations performed by the circuitry of FIG. 1, the frequency of pulses appearing at line 12 is equal to $(N/1000) \times f$ where the input frequency at line 10 is 100 $f$. The frequency of the signal appearing at line 14, on the other hand, is equal to $[1 - (N/1000)]f$.

The pulse train appearing at line 12 is coupled by a stepper driver 56 to a stepping motor 58 which drives pump A. The stepper driver 56 converts the pulse signal appearing at line 12 into a signal suitable for driving the stepping motor 58. The stepping motor 58 itself responds to the signals from the stepper driver 56 to drive the pump at a speed which is proportional to the frequency of the pulse signal appearing at line 12. This causes pump A to pump fluid A at a rate proportional to the frequency of the pulse train appearing on line 12. In a similar manner, the pulses at line 14 are converted by a stepper drive 60 which is coupled to a stepping motor 62 which powers pump B. Pump B, however, operates at a speed which is proportional to the frequency of the pulse train appearing on line 14. Since the number of pulses appearing at lines 12 and 14 over a given time period is a constant, the rate of flow of fluid A and fluid B over the same period of time is also a constant. Accordingly, the circuitry of FIG. 1 is operative to control the total flow of fluids A and B in conduit 20 while selecting the percentage of each fluid in the total by setting the selector means 22.

FIG. 2 is an exemplary circuit diagram for the electronic circuitry shown in the block diagram of FIG. 1. The circuitry of FIG. 2 includes an adjustable clock pulse generator 100 for producing a square wave signal at its output 102 having a frequency of 100$f$. This square wave signal is coupled to the clock pin 9 of three decade rate multipliers 104, 106 and 108. In the embodiment shown in FIG. 2, these decade rate multipliers 104, 106 and 108 each comprise a Texas Instruments SN74167 synchronous decade rate multiplier. Other synchronous decade rate multiplier circuit types are available and they may be substituted, with appropriate wiring modification, into the circuit of FIG. 2. Switches 1, 2 and 3 are respectively coupled to the decade rate multipliers 104, 106 and 108 and produce, in cooperation with the resistors and power supply coupled thereto, a binary coded signal at the input pins 2, 3, 14 and 15 of each rate multiplier 104, 106 and 108 which corresponds to the decimal digit to which the switch is set. Each switch 1, 2 or 3 is operative along with the coupled resistors and power supply to select a decimal digit from between zero and nine and it places a corresponding binary coded decimal signal pattern, representative of either a logic 1 or 0, onto the input pins 2, 3, 14 and 15 of the coupled rate multiplier which is utilized thereby to produce a corresponding number of pulses at its output pin 5 for every ten pulses appearing at its input pin 9 at times when the rate multiplier is enabled by a logic 0 (low) signal on pin 11. For rate multiplier 104, the signal at pin 6 equals pin 5.

Figure 3B:
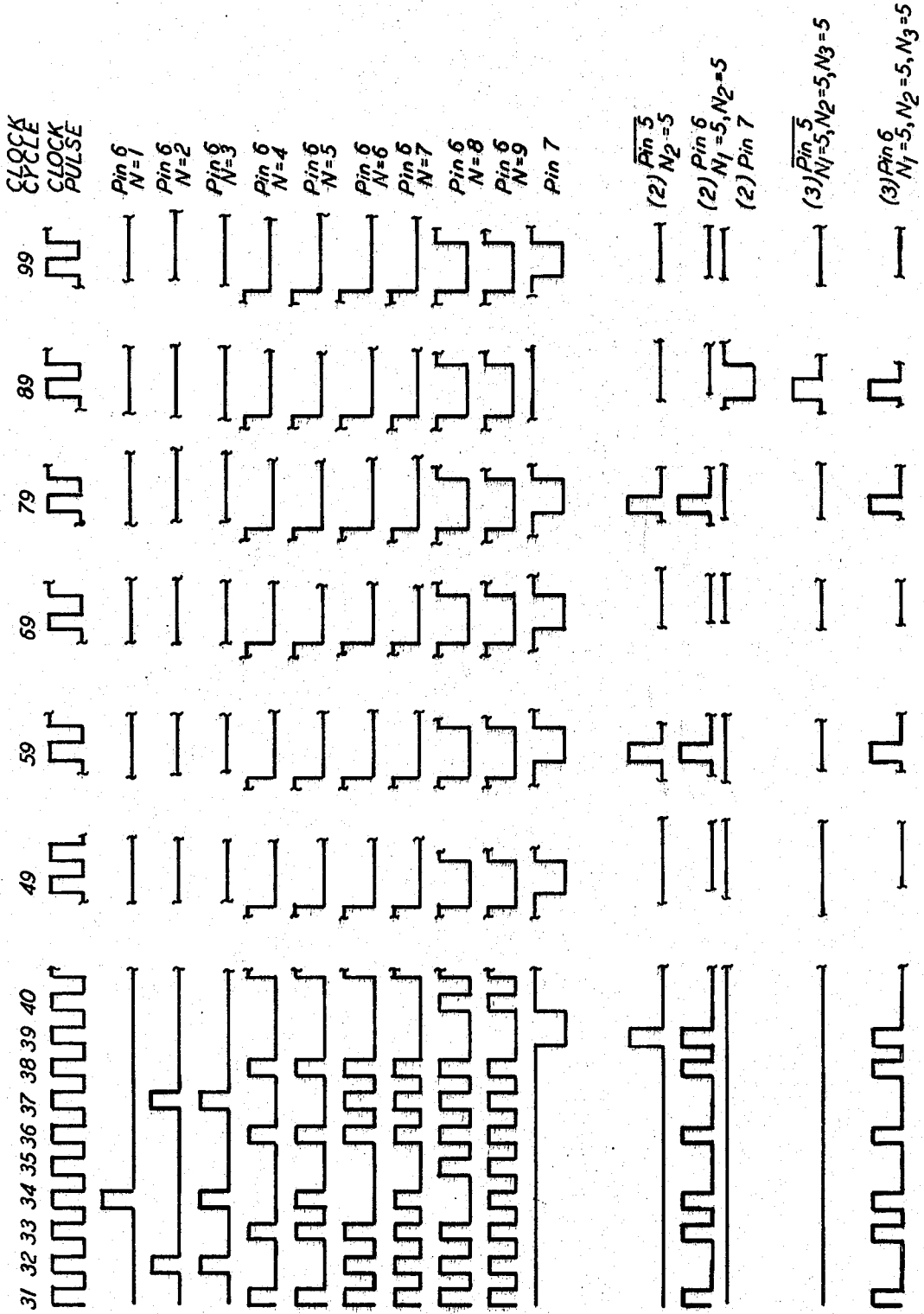

FIGS. 3A and 3B show a pulse diagram for various pins in the 3 cascaded decimal rate multipliers 104, 106, and 108 of FIG. 2. Of particular interest, however, is the output at pin 5 of decimal rate multiplier 104 which is a function of the setting for digit switch 1. As viewed in FIG. 3A, the pulse train labelled clock is applied to pin 9 of the rate multiplier 104. When switch 1 is set to zero, no pulses appear at the output pin 5. On the other hand, if the digit switch is set to any other number between zero and nine, the output pulse pattern at pin 6 is shown for each possible digit to which switch 1 can be set. For example, when digit switch 1 is set to a one, one pulse occurs at the output pin 6 for every 10 pulses appearing at pin 9 while the rate multiplier 104 is enabled. Since pins 4, 8, 10, 11 and 13 are always held at ground potential, the rate multiplier 104, in accordance with the operation for the Texas Instruments SN74167, is continually enabled. Therefore, one pulse appears at pin 6 for every 10 appearing at pin 9 and it appears during the fourth clock cycle out of every 10 clock cycles.

On the other hand, when switch 1 is set to five, for example, five pulses appear at output pin 6 for every 10 pulses input to pin 9. Consequently, the setting of switch 1 defines the number of pulses appearing at pin 5 for every 10 pulses input to pin 9 of rate multiplier 104.

It should be noted that the specified decade rate multiplier 104 never produces an output pulse at pin 6 during each ninth clock cycle out of 10 clock cycles appearing at pin 9. This aspect of the specified module is exploited by the cascade configuration of FIG. 2 in that the enable signal, appearing at pin 7 of decade rate multiplier 104 goes to ground potential only during the ninth clock cycle during which decade rate multiplier 104 is enabled. Accordingly, decade rate multiplier 106 is enabled by the ground connection at pins 10 and 11 every ninth clock cycle out of ten appearing at decade rate multiplier 104. As such, a pulse may be produced at pin 5 of decade rate multiplier 106 only during one clock cycle out of every 10 for which the decade rate multiplier 104 is enabled.

The decade rate multiplier 106 responds to the setting of switch 2 by producing a corresponding number of pulses at its output pin 5 for every ten pulses appearing at pin 9 while pins 10 and 11 are at ground potential. In other words, a pulse may appear at pin 5 of decade rate multiplier 106 during the ninth, 19, the 29 etc. clock cycles of the signal appearing at pin 9 of the decade rate multiplier 104.

Since decade rate multiplier 106 is the same circuit type as that for decade rate multiplier 104, it functionally operates in the same manner and, therefore, if switch 2 is set to a five, a pulse is produced at pin 5 of decade rate multiplier 106 during the ninth clock cycle. Other pulses are produced at pin 5 of decimal rate multiplier 106 during clock cycles 29, 39, 59 and 79 so that out of 100 pulses appearing at pin 9 of rate multiplier 106, five pulses are produced at its output pin 5. If digit switch 2 were set to another value, a corresponding number of pulses would be produced at output pin 5 of the decade rate multiplier 106 for every 100 clock cycles on line 102.

By reason of circuitry internal to the decade rate multiplier 106, the output signal from pin 5 of decade rate multiplier 104 which couples to pin 12 of rate multiplier 106 also appears at pin 6 of decade rate multiplier 106 NANDed with the output pulses appearing at pin 5 of the decade rate multiplier 106. These pulses are inverted by an inverter 110 whose output forms the input to pin 12 of the decade rate multiplier 108. As such, a pulse appears at pin 12 at decade rate multiplier 108 during every clock cycle that a pulse appears at pin 5 of either decade rate multiplier 104 or 106.

By reason of the fact that the enable output 7 of the decade rate multiplier 106 is coupled to pins 10 and 11 of the decade rate multiplier 108, the decade rate multiplier 108 is enabled by the preceeding decade rate multiplier 106 during the 89th clock period, as indicated in FIG. 3B. Consequently, the decade rate multiplier 108 is enabled during one clock cycle out of every one hundred clock cycles at its clock input pin 9. A decade rate multiplier 108 is also enabled, although not indicated in FIGS. 3A or 3B during clock periods 189, 289, 389, etc. As such, decade rate multiplier 108 produces the number of pulses identified by the digit in switch 3 at its output pin 5 for every 1,000 pulses input to pin 9 thereof.

By reason of circuitry internal to decade rate multiplier 108, the input pulses appearing at pin 12 are NANDed with the pulses appearing at pin 5 so that a pulse appears at pin 6 of decade rate multiplier 108 during every clock cycle that a pulse is generated at pin 5 of either decade rate multiplier 104, 106 or 108. Therefore, the pulse pattern appearing at pin 6 of decade rate multiplier 108 comprises a first intermediate pulse train with the number of pulses over 1000 clock cycles at line 112 equalling the sum of the pulses appearing at output pin 5 of each decade rate multiplier 104, 106 and 108. A diagram for the summing circuitry, both internal and external to the modules 104, 106 and 108, is shown in detail in FIG. 2. An alternative thereto, however, is simply a 3 input NAND gate coupled to output pin 5 of each decade rate multiplier 104, 106 and 108 where the NAND gate output connects to input pin 1 of counter 114. The output line 112 is disconnected.

In operation, the circuitry described so far is operative to produce a first intermediate pulse train with N pulses on the line 112 for every 1,000 pulses appearing on line 102 where N is a decimal number having three digits $N_1$, $N_2$ and $N_3$ and switches 1, 2 and 3 are respectively set to values $N_1$, $N_2$, and $N_3$. This first intermediate pulse train is coupled to the input of a pulse counter 114 whose function is described below in greater detail.

Referring again to FIG. 2, a difference circuit shown within dotted line 116 couples to the clock pulse generator and the output signals appearing at pin 5 of each decade rate multiplier 104, 106 and 108. The difference circuit 116 has an inverter 118 for inverting the clock pulses on line 102 thereby producing an inverted clock pulse signal on line 120 which forms one input to a NAND gate 122. The other three inputs to NAND gate 122 couple directly to output pin 5 from each decade rate multiplier 104, 106 and 108. The output of the NAND at 122 is inverted by an inverter 124 and coupled to a line 126 to a pulse counter 128 whose functon is described below in greater detail.

Functionally a pulse is produced on the line 126 during every clock cycle that a pulse does not appear at any output pin 5 from either decade rate multiplier 104, 106 or 108. As such, for every 1,000 pulses appearing on line 102 from the clock pulse generator 100, 1,000 pulses are produced on the lines 112 and 126 with N pulses appearing on line 112 and (1,000 - N) pulses appearing on line 126. Additionally, the pulses appearing on line 112 always occur during different clock cycles than the clock cycles during which pulses appear on line 126.

The pulse counters 114 and 128 each comprise a spectral purification means to produce a single pulse at their output for every 100 pulses appearing at their input. For the particular embodiment shown in FIG. 2, each counter is comprised of two decade divide circuits connected in cascade where each divider circuit comprises a Texas Instruments SN7490 although other equivalent circuit types may be substituted therefor. Each pulse counter 114 or 128 may also comprise any other circuit for dividing the number of pulses input thereto by a given number. As such, when the input frequency on line 102 is equal to $Qf$, the frequency of pulses appearing at the line labelled $f_A$ is $(N/1000) \times (Q/100) \times f$. The frequency of pulses appearing at the line labelled $f_B$ is $[1 - (N/1000)] (Q/100) \times f$. Accordingly, the sum of pulses appearing on the lines labelled $f_A$ and $f_B$ is a constant over a given period time and directly related to the frequency of the clock pulse generator 100. The number of pulses appearing at the line labelled $f_A$ over the fixed time period, however, is selected by the setting of the three switches 30, 32 and 34 respectively to the value of $N_1$, $N_2$ and $N_3$.

Should greater frequency stability be desired, however, a third divide by ten circuit can couple in cascade with the other two counters 114 or 128 so as to divide the incoming pulse train by 1,000. To achieve the same pulse rate at the output of the counters 114 or 128 where it divides the input by 1,000, the pulse rate of the clock pulse generator 100 must be increased to equal $1,000f$.

Greater output frequency stability can be achieved by adding still more division steps to each counter 114 and 128.

Should further resolution of the number N be desired, further decade rate multipliers can be coupled in cascade to those shown in FIG. 2 and these further decade rate multipliers would be coupled into the remainder of the circuitry in a manner substantially identical to that shown for the decade rate multipliers in FIG. 2. In this manner, if one further decade rate multiplier were included, the number N would comprise a four decimal digit number and the rate of pulses appearing at the output line labelled $f_A$ would be $(N/10,000)f$ where the frequency of pulses from the clock pulse generator 100 is $100f$ and the pulse rate on line 126 would be $[1 - (N/10,000)]f$.

From the foregoing description, it is evident that the circuitry of FIG. 2 is operative to produce two output pulse trains at lines labelled $f_A$ and $f_B$ where the percent of pulses in pulse train A as compared to the number of pulses in both pulse train A and B over a fixed time period is controlled by the number N in the selector means comprising switches 1, 2 and 3. The total number of pulses in pulse train A and B over a fixed time period is controlled by the pulse rate of generator 100 and by the pulse counters 114 and 128. For the illustrative embodiment of the invention, therefore, the total flow rate of fluid A and B is controlled by the frequency of clock pulses from generator 100 and the percentage of each constituent (fluid A and fluid B) in the total flow of both fluid A and B is controlled by the number N.

While the foregoing description has emphasized an exemplary embodiment of the invention, those of skill in the art will recognize other applications for the new two component pulse rate synthesizer. In addition, alternative circuit configurations for implementing the described function of specific circuit elements will readily occur to skilled circuit designers. For example, the BCD digital rate multipliers specified above may be replaced by binary rate multiplier circuits. The selector means associated with such binary rate multiplier must be compatible therewith. The output pulse train produced by this alternative configuration has a constant number of pulses produced over a given time period with the proportion in each of two pulse trains being selectable.

It should be noted that pumps such as pump A and pump B of FIG. 1 are frequently of the same type and nominally pump fluid therethrough at the same rate when driven at the same speed. As such pumps are mechanical devices, the tolerances to which they can be manufactured does in actuality cause one pump to pump fluids at a slightly different rate than another pump even when driven at the same speed. As such, the configuration of FIG. 1 may not produce the same flow of fluid A and fluid B.

Figure 5:
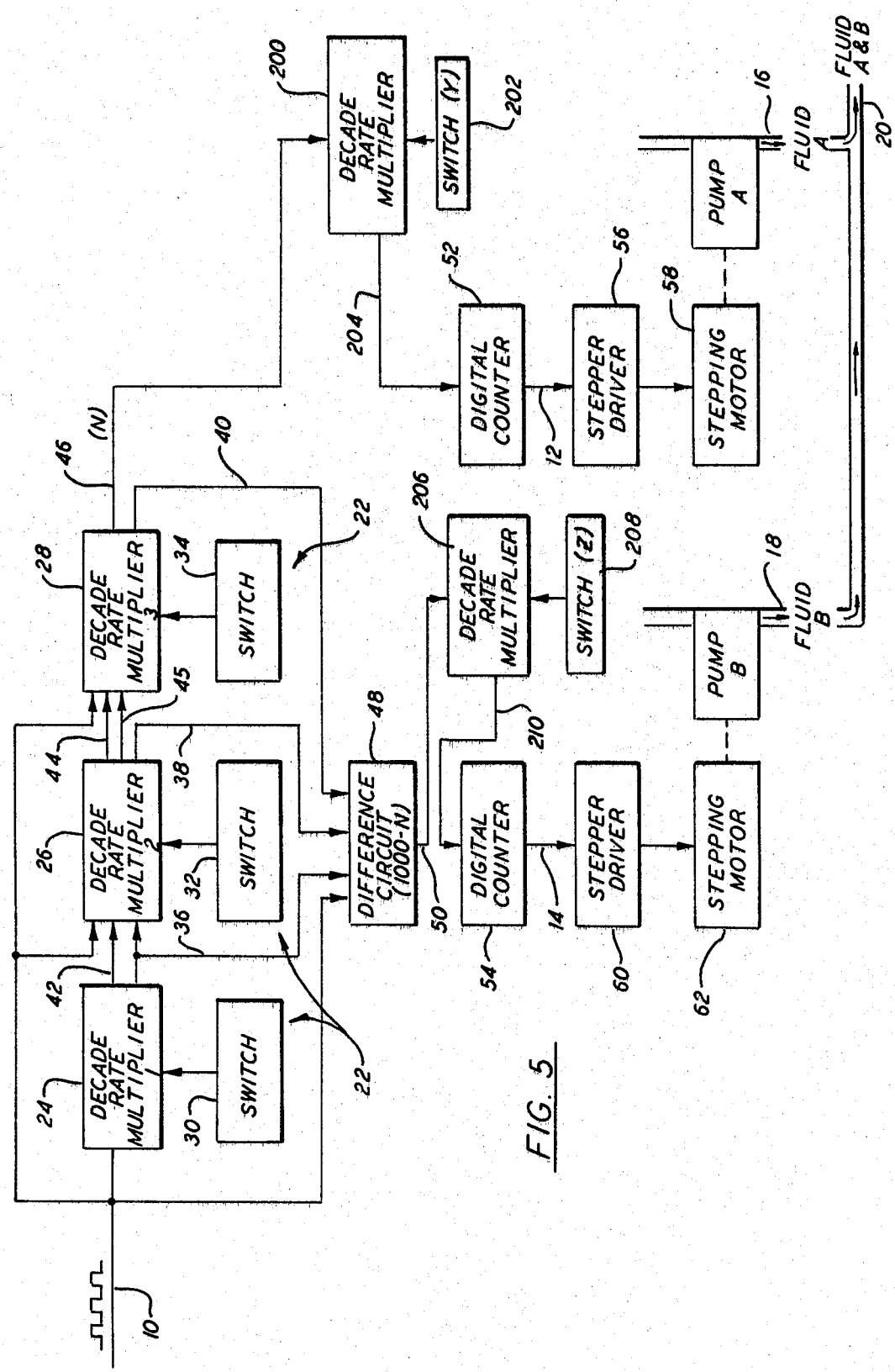
FIG. 5 is a block diagram of a pulse generator of the type shown in FIG. 1 additionally including circuitry to adjust the flow rate of each pump to compensate for slight physical differences between the pumps.

FIG. 5 shows alternative embodiment of the present invention which includes circuitry for changing the rate of pulses applied to the stepper driver circuits 56 and 60 thereby causing the respectively coupled stepping motor 58 and 62 to rotate at a slightly different speed than is achieved by the circuit of FIG. 1 thus causing the respectively coupled pump A and pump B to pump at a different rate than for the circuit of FIG. 1. The capability to modify the individual flow rate for the two pumps permits the circuit of FIG. 5 to maintain a truly constant total flow rate of two fluids while selectively being able to set the flow rate of one such fluid.

The circuitry of FIG. 1 is modified in FIG. 5 by breaking the output line 46 between the decade rate multiplier 28 and the digital counter 52 and inserting a decade rate multiplier 200 (similar to circuits 24 and 26) which is coupled to a selector switch 202 arrangement similar to switches 30 and 32. The output of the decade rate multiplier 200 is coupled by an output wire 204 to the digital counter 52. In a similar manner, the output line 50 between the difference circuit 48 and the digital counter 54 is broken and coupled to the input of yet another decade rate multiplier 206 which is coupled to a selector switch 208. The output of the decade rate multiplier is coupled by an output wire 210 to the input of the digital counter 54.

The function of the additional decade rate multipliers 200 and 206 is to modify the pulse string which is coupled to each digital counter 52 and 54. Assuming for the moment that the decade rate multiplier 200 is identical in function to the decade rate multiplier 24, if the switch 202 is set to a digital number Y (a digital number between 0 and 9), for every ten pulses appearing on the output wire 46 which couples to the decade rate multiplier 200 input, Y pulses will appear on its output wire 204. Accordingly, the decade rate multiplier 200 functions to reduce the average pulse rate appearing at the output of counter 52. In a similar manner, the decade rate multiplier 206 is operative to reduce the average pulse rate of pulses appearing at the input to the digital counter 54.

In the preferred arrangement of the present invention, however, the decade rate multipliers 200 and 206 do not comprise a single stage decade rate multiplier such as decade rate multiplier 24 but in fact preferrably comprise two or more cascade connected decade rate multipliers such as for the arrangement shown for decade rate multiplier 24 and 26. Accordingly, the switches 202 and 208 actually comprise a plurality of decade switches with each switch being coupled to one decade rate multiplier circuit such as switch 30 is coupled to decade rate multiplier 24.

Accordingly, if decade rate multiplier 200 comprises two stages and the switch 202 correspondingly has two selectable decade switches, the number Y which may be set by the switch 202 can range from 0 to 99. The function thereof is to permit Y pulses to appear on the output wire 204 for every 100 pulses appearing at its input as coupled thereto by the output wire 46.

The preferred arrangement according to the present invention for the decade rate multiplier 206 also comprises two cascade coupled decade rate multiplier circuits and the switch 208 includes two decade switches so that a digital number Z between 0 and 99 can be selected thereby as well. Accordingly, for every 100 pulses appearing on the output wire 50, Z pulses appear on the output wire 210 from the decade rate multiplier 206.

Those of skill in the art will readily realize that the above-mentioned functions for the decade rate multipliers 200 and 206 and their coupled switch selector switches 202 and 208 can be accomplished by circuitry such as for the decade rate multipliers 24, 26 and switches 30 and 32 wherein the input wire corresponds to wire 10 and the output wire corresponds to output line 45. Other circuit configurations may also be used to accomplish the desired objective.

In the normal operation of the circuitry according to FIG. 5 as opposed to the operation of the circuitry according to FIG. 1, the frequency of pulses appearing at the input of the circuitry of FIG. 5 is preferrably higher than the frequency of pulses appearing at the input line 10 for the circuit of FIG. 1. The reason for this input frequency difference will become more apparent from the following discussion. Assuming that the input frequency for the circuit of FIG. 1 remains $100f$ and the input frequency on line 10 for the circuitry of FIG. 5 is $117.6f$. Also assume that the switches 30, 32 and 34 are set to a number N which equals 800. Accordingly, for every 1000 pulses appearing on input line 10 of FIG. 1, 800 pulses will appear at the output line 46. For the circuitry of FIG. 5, the same switches 30, 32 and 34 are set there as for FIG. 1, however, the frequency of signals appearing at the output line 46 is increased. Accordingly, in the same time period that 1000 pulses were input on line 10 in FIG. 1, about 1176 pulses appeared at the input line 10 of FIG. 5. According to the operation of the circuitry of FIG. 1 which is common to that of FIG. 5, approximately 940 pulses will appear at output line 46 during the same time period that 800 pulses appeared at output line 46 of FIG. 1.

Assume further that number Y to which the selector switch 202 is set is equal to 85. Accordingly, the decade rate multiplier 200 will produce 85 pulses on its output wire 204 for every 100 pulses at its input from the line 46. Consequently, during the time period when 940 pulses appear on output line 46 in FIG. 5 when the switches 30, 32 and 34 are preset as indicated above, approximately 799 pulses will appear at the output line 204 from the decade rate multiplier 200. Accordingly, the circuitry of FIG. 5 when the frequency on the input line 10 is raised to $117.6f$ and the selector switch 202 is set to 85 causes approximately the same number of pulses to appear at the input of the digital counter 52 during the same period of time as appear at the input to the digital counter 52 for the circuit of FIG. 1, assuming that the selector switches 30, 32 and 34 of both circuits are set to the same digital value. As such, the circuitry of FIG. 5 can be made to produce the same number of pulses during the same period of time at the input to the digital counter 52.

The same analysis can be applied to the circuitry of FIGS. 1 and 5 with respect to the decade rate multiplier 206. Accordingly, when the decade rate multiplier 206 has its coupled switch 208 set so that Z is 85, almost the exact same number of pulses appear at the output line 210 during a given period of time as appear on the output line 50 of FIG. 1, assuming that the selector switches 30, 32 and 34 of both circuits are set to the same value. Accordingly, by properly raising the frequency of pulses appearing at the input line 10 of FIG. 5 and by selecting the proper digital value Y and Z for the setting of switches 202 and 208, the circuitry of FIG. 5 can be made to function substantially identically to the circuitry of FIG. 1.

The circuitry of FIG. 5, however, can also be made to increase or decrease the number of pulses appearing during a given period of time at the input to either digital counter 52 or 54 as compared to the number of pulses appearing at the input to counters 52 or 54 when switches 200 and 206 are each set to 85. Assuming for the moment that the selector switches 30, 32 and 34 remain set to 800 and the input frequency at the input line 10 is $117.6f$, if the selector switch 202 is set to 90, approximately 846 pulses will appear at the output line 204 during the same time period that 800 pulses appeared there when the selector switch 202 was set to 85. As such, by adjusting the value of the selector switch 202 upwardly from 85, the number of pulses appearing on output line 204 during a given period of time is greater than appear on line 204 when the switch 202 is set to 85. As such, a higher pulses rate appears at the input to the stepper driver 56 and 58 in accordance with the operation of the invention as heretofore described. This causes a corresponding increase of the speed of pump A thereby increasing the rate of flow of fluid A through conduit 16.

By a similar analysis, if the switch 202 is set below 85, the average pulse rate appearing on the output line 204 is lower than when switch 202 is set to 85 thereby causing a reduction in the pulse rate appearing at the input to the stepper driver 56 which correspondingly causes a reduction in the pumping rate of pump A. As such, by adjusting the setting of switch 202, the pumping rate of pump A is somewhat increased or decreased depending on the setting of the switch 202 as compared to the pumping rate achieved by the circuitry of FIG. 1 when switches 30, 32 and 34 of both FIG. 1 and FIG. 5 are set to the same value. This observation, of course, assumes that the frequency of pulses appearing at the input line 10 of FIG. 5 is greater than the frequency of pulses appearing on line 10 of FIG. 1. As such, the pumping rate of an individual pump can be slightly modified by the additional circuitry of FIG. 5 thereby permitting the flow rate through the conduits 16 and 18 to be precisely adjusted to compensation for physical differences between pumps A and B so as to assure that the total pumping rate of fluids A and B is always equal to a constant. This feature is particularly advantageous, as is readily recognized by those of skill in the art, for permitting precise control of the combined flow rate of fluids A and B in separate systems or even in one system where a pump must be replaced by another one having slightly different pumping characteristics.

Those of skill in the art readily recognize that the circuitry of FIG. 5 may be further modified from that described by, for example, permitting the decade rate multipliers 200 and 206 to have greater than two stages with a corresponding increase in the number of stages for the coupled switches 202 and 208. By further increasing the number of stages for the decade rate multipliers 200 and 206, more precise adjustment of the pumping rate of the coupled pumps A and B can be achieved.

The foregoing and other modifications to the circuitry described above can be made without departing from the spirit and scope of the invention as defined in the following claims.

What is claimed is:

1. A pulse generator for producing two pulse trains where the sum of pulses in both pulse trains in a constant over a fixed time period and the pulse rate of one train is selectable, the generator comprising, in combination:

a source of clock pulses with one clock pulse occurring per clock cycle;

a plurality of selector means each selectively providing a unique signal representative of a decimal digit correlated to the pulse rate of one pulse train;

a plurality of synchronous decade rate multipliers each coupled to said source of clock pulses and to one selector means to receive unique signals therefrom, said decade rate multipliers being connected in cascade so that the first decade rate multiplier is operative during each clock cycle and capable of producing an output pulse during nine out of every ten clock cycles, each successive decade rate multiplier is operative during only the one clock cycle that the previous rate multiplier cannot produce an output pulse, each said decade rate multiplier producing X pulses at its output for each ten clock cycles that it is operative where X corresponds to the setting of the selector means coupled thereto;

summing means responsive to the output pulses from each said decade rate multiplier to produce a pulse in a first intermediate pulse train for each output pulse from any decade rate multiplier;

difference means responsive to said clock pulses and the output from each said decade rate multiplier to produce a second intermediate pulse train having a pulse whenever a clock pulse occurs in the absence of an output pulse from any said decade rate multiplier; and a first pulse counter responsive to said first intermediate pulse train and a second pulse counter responsive to said second intermediate pulse train, each said pulse counter being operative to produce one output pulse in a pulse train for every N intermediate pulses input thereto, the output of said first pulse counter comprises a first output pulse train and the output of said second pulse counter comprises a second output pulse train, where N is the whole decimal number.

2. The pulse generator of claim 1 wherein the rate of said source of clock pulses is adjustable so that the constant sum of said two output pulse trains is adjustable.

3. The pulse generator of claim 1 wherein each said selector means includes means to actuate a plurality of output lines to place a binary coded signal thereon corresponding to the digit to which it is set.

4. The pulse generator of claim 1 wherein said difference means comprises, in combination:

a first inverter to invert said clock pulses to produce inverted clock pulses; and a NAND gate responsive to said first inverter and to the output pulses from each said decade rate multiplier to produce output pulses comprising the inverted said second intermediate pulse train.

5. The pulse generator of claim 1 additionally including pump means responsive to said first output pulse train to pump a first fluid at a rate correlated to the frequency of pulses in said first output pulse train and including means responsive to said second output pulse train to pump a second fluid at a rate correlated to the frequency of pulses in said second output pulse train.

6. The pulse generator of claim 1 wherein said plurality of selector means includes means responsive to changes in at least one external condition to dynamically change the decimal digit signal produced thereby.

7. A control circuit for controlling the rate of flow of two fluids so that the total rate of flow of the two fluids is a constant while the ratio of one fluid flow rate to the other is adjustable, the control circuit comprising, in combination:

a pulse generator producing clock pulses at an adjustable rate wherein the clock pulse rate is correlated to the total flow rate of the two fluids;

selector means for producing signals representative of a plurality of decimal digits correlated to the flow rate of one fluid;

a plurality of synchronous decade rate multipliers connected in cascade and responsive to said pulse generator and said selector means, each decade rate multiplier producing output pulses correlated to the signals representative of one said decimal digit;

summing means responsive to each output from each said decade rate multiplier to produce a first intermediate pulse train with one pulse for each pulse input to said summing means;

difference means responsive to said clock pulses and each said decade rate multiplier to produce a second intermediate pulse train having a pulse occurring at the time each clock pulse occurs in the absence of an output pulse from any said rate multiplier;

first spectral purifying means to produce one pulse in a first train of output pulses for every N pulses in said first intermediate pulse train where N is a whole decimal number;

second spectral purifying means to produce one pulse in a second train of output pulses for every N pulse in said second intermediate pulse train;

first pump means responsive to said first train of output pulses to pump a first fluid at a rate proportional to the pulse rate of said first train of output pulses; and second pump means responsive to said second train of output pulses to pump a second fluid at a rate proportional to the pulse rate of said second train of output pulses.

8. The control circuit of claim 7 wherein said summing circuit logically ORs the output pulses from each said rate multiplier to produce said first intermediate pulse train.

9. The control circuit of claim 7 wherein said difference means comprises: an inverter responsive to said clock pulses to produce inverted clock pulses;

a NAND gate responsive to the output pulses from each said rate multiplier and to said inverse clock pulses to produce an inverse second intermediate pulse string; and an inverter responsive to said inverted second intermediate pulse string to produce said second intermediate pulse string.

10. The control circuit of claim 7 wherein said first and said second spectral purifying means each comprise a pulse divider circuit for dividing the pulse train input thereto by N.

11. The control circuit of claim 7 wherein said selector means includes means responsive to an external condition to dynamically produce signals representative of that changing condition which comprises said signals representative of a plurality of decimal digits.

12. The control circuit of claim 7 additionally including a second selector means to produce a unique signal for each digit in a second number Y having $q$ digits therein correlated to adjustment of the flow rate of said first pump means;

a second plurality of decade rate multipliers coupled to said summing means and to said second selector means to produce modified first intermediate pulse train having Y pulses therein for every $10^q$ pulses input thereto, said modified first intermediate pulse train being coupled to said first spectral purifying means in place of said first intermediate pulse train.

13. The control circuit of claim 12 additionally including a further selector means to produce a unique signal for each digit in a number Z having $q$ digits therein correlated to adjustment of the rate of flow of said second pump means; and a further plurality of decade rate multipliers coupled to said difference means and to said further selector means to produce a modified second intermediate pulse train having Z pulses therein for every $10^q$ pulses input thereto, said modified second intermediate pulse train being coupled to said second spectral purifying means in place of said intermediate pulse train.

14. The control circuit of claim 7 additionally including a further selector means to produce a unique signal for each digit in a number Z having $q$ digits therein correlated to adjustment of the rate of flow of said second pump means; and a further plurality of decade rate multipliers coupled to said difference means and to said further selector means to produce a modified second intermediate pulse train having Z pulses therein for every $10^q$ pulses input thereto, said modified second intermediate pulse train being coupled to said second spectral purifying means in place of said second intermediate pulse train.

15. A pulse generator for producing two pulse trains A and B comprising, in combination:

a clock pulse generator for producing clock pulses at a rate QF where Q is a number and F is a pulse rate;

P selector means for selecting a number N where P corresponds to the number of digits in the number N where $N_1$ is the most significant digit and $N_p$ is the least significant digit;

P pulse rate changing circuits coupled in cascade where each said pulse rate changing circuit is coupled to said clock pulse generator and to one said selector means, each successive pulse rate changing circuit producing $N_q$ pulses for every $10^q$ clock pulses where $q$ corresponds to the digit significance of the number N where $q=1$ for the most significant digit and $q=P$ for the least significant digit;

means for summing the pulses produced at each said pulse rate changing circuit to produce a first output pulse train wherein the number of pulses produced thereby equals N for every $10^p$ clock pulses;

difference means responsive to said clock pulse generator and each said pulse rate changing circuit to produce a second output pulse train with $(10^P-N)$ pulses for every $10^P$ clock pulses;

first division means to divide said first output pulse train by Q to produce pulse train A with an output frequency $f_A$ equal to $F \times N$; and second division means to divide said second output pulse train $10^P$ by Q to produce pulse train B with an output frequency $f_B$ equal to $F [1 - (N/10^p)]$.

16. The pulse generator of claim 15 wherein said clock pulse generator includes means to vary the rate of pulses produced thereby.

17. The pulse generator of claim 15 wherein said summing means comprises a circuit to produce a pulse for each pulse produced by any said pulse rate changing circuit.

18. The pulse generator of claim 15 wherein said difference means includes:

an inverter responsive to said clock pulse generator to produce inverted clock pulses;

a NAND gate responsive to said inverted clock pulses and to said pulses from each said pulse rate changing circuit for producing a pulse whenever a pulse is not produced at any pulse rate changing circuit at the time of a pulse from said clock generator.

19. The pulse generator of claim 15 wherein said difference means includes a circuit to produce a pulse at the time of a clock pulse if no pulse is produced at that time by any said pulse rate changing circuit.

20. The pulse generator of claim 15 additionally including pump means responsive to pulse train A to pump a fluid at a rate proportional to the frequency $f_A$ of pulses in pulse train A.

21. The pulse generator of claim 15 additionally including pump means responsive to pulse train B to pump a fluid at a rate proportional to the frequency $f_B$ of pulses in pulse train B.

22. The generator of claim 15 additionally including:

first pump means responsive to pulse train A to pump a first fluid at a rate proportional to the frequency $f_A$ of pulses in pulse train A; and second pump means responsive to pulse train B to pump a second fluid at a rate proportional to the frequency $f_B$ of pulse train B.

23. The pulse generator of claim 22 wherein said clock pulse generator includes means to vary the rate of pulses produced thereby to adjust the total flow rate of said first and said second fluid.

24. The pulse generator of claim 15 wherein said P selector means includes means responsive dynamically to an external condition to vary the number N in response to changes in said external condition.

25. The pulse generator of claim 15 additionally including an adjustable pulse division means for selectively producing from said first output pulse train a modified first output pulse train having no more than N pulses every $10^P$ clock pulses, said modified first output pulse train being coupled to said first division means in place of said first output pulse train.

26. The pulse generator of claim 15 additionally including an adjustable pulse division means for selectively producing from said second output pulse train a modified second output pulse train having no more than $(10^P-N)$ pulses every $10^P$ clock pulses, said modified second output pulse train being coupled to said second division means in place of said second output pulse train.

27. A pulse generator for producing two pulse trains suitable for controlling the operation of two pumps so that the total flow rate of both pumps remains a constant while the rate of one pump is selectable, the generator comprising, in combination:

a source of clock pulses with one clock pulse occurring per clock cycle;

a plurality of selector means each selectively providing an unique signal representative of a decimal digit correlated to a first pulse rate;

a plurality of first decade rate multipliers each coupled to said source of clock pulses and to one selector means to receive unique signals therefrom, said first decade rate multipliers being connected in cascade so that the first decade rate multiplier is operative during each clock cycle and capable of producing an output pulse during nine out of every ten clock cycles, each successive first decade rate multiplier is operative during only the one clock cycle that the previous first decade rate multiplier cannot produce an output pulse, each said first decade rate multiplier being capable of producing X pulses at its output for each ten clock cycles that it is operative where X corresponds to the setting of the selector means coupled thereto;

summing means responsive to the output pulses from each said first decade rate multiplier to produce a pulse in a first intermediate pulse train for each output pulse from each first decade rate multiplier;

difference means responsive to each said clock pulse and said output pulses from each first decade rate multiplier to produce a second intermediate pulse train having a pulse during each clock cycle occurring in the absence of a pulse from any said first decade rate multiplier;

at least one second decade rate multiplier coupled to first intermediate pulse train and to a selector means for each said second decade rate multiplier to receive unique signals therefrom, said second decade rate multipliers producing a third intermediate pulse train having Y pulses for each $10^p$ pulses in the first intermediate pulse train where Y corresponds to the setting of the selector means coupled to said second decade rate multipliers and $p$ corresponds to the number of said second decade rate multipliers; and at least one third decade rate multiplier, each coupled to said second intermediate pulse train and to a selector means to receive unique signals therefrom, said third decade rate multipliers producing a fourth intermediate pulse train having Z pulses for every $10^q$ pulses in said second intermediate pulse train where Z corresponds to the setting of the selector means coupled to said third decade rate multiplier and where $q$ equals the number of third rate multipliers.

28. The pulse generator of claim 27 additionally including a first pulse counter responsive to said third intermediate pulse train and a second pulse counter responsive to said fourth intermediate pulse train, each said pulse counter producing one pulse at its output for each N pulses input thereto where N is a whole decimal number.

29. The pulse generator of claim 28 additionally including a first pump means responsive to said first pulse counter and a second pump means responsive to said second pulse counter, each said pump means being operative to pump a fluid at a flow rate related to the rate of pulses received from the pulse counter coupled thereto.

30. The pulse generator of claim 27 wherein said source of clock pulses is adjustable to produce clock pulses at an adjustable rate.

* * * * *